US012778226B2

(12) United States Patent
Chen

(10) Patent No.: US 12,778,226 B2
(45) Date of Patent: Nov. 3, 2026

(54) HEATING SHAWL

(71) Applicant: JingWeiLianHe (Hong Kong) Technology Co., Limited, Hongkong (CN)

(72) Inventor: Xin Chen, Hongkong (CN)

(73) Assignee: JingWeiLianHe (Hong Kong) Technology Co., Limited, Hongkong (CN)

( * ) Notice: Subject to any disclaimer, the term of this patent is extended or adjusted under 35 U.S.C. 154(b) by 0 days.

(21) Appl. No.: 18/828,187

(22) Filed: Sep. 9, 2024

(65) Prior Publication Data

US 2026/0068973 A1 Mar. 12, 2026

(51) Int. Cl.

| | |
|---|---|
| ***A41D 23/00*** | (2006.01) |
| ***A41D 13/005*** | (2006.01) |
| ***A61F 7/02*** | (2006.01) |

(52) U.S. Cl.

CPC ......... *A41D 23/00* (2013.01); *A41D 13/0051* (2013.01); *A41D 2400/12* (2013.01); *A61F 2007/0233* (2013.01)

(58) Field of Classification Search

CPC .............. A41D 13/005; A41D 13/0051; A41D 13/02; A41D 13/0512; A41D 2400/10; A41D 2400/12; A45D 44/08; A61F 2007/0233; H05B 3/342; H05B 3/345; H05B 3/347; H05B 2203/036

See application file for complete search history.

(56) References Cited

U.S. PATENT DOCUMENTS

| | | | | |
|---|---|---|---|---|
| 2,794,985 A * | 6/1957 | Brennish | A45D 44/08 2/48 |
| 5,138,133 A * | 8/1992 | Sakurada | H05B 3/36 219/528 |
| 7,000,682 B2 * | 2/2006 | Chambers | A41D 13/005 607/104 |
| 9,894,944 B2 * | 2/2018 | Brooks | A41D 13/0051 |

(Continued)

FOREIGN PATENT DOCUMENTS

| | | |
|---|---|---|
| CN | 203735515 U * | 7/2014 |
| CN | 204501192 U * | 7/2015 |

(Continued)

OTHER PUBLICATIONS

Amazon.com Listing for Graphene-Infused Heating Pad 3X, with first available date Aug. 25, 2023, retrieved at https://www.amazon.com/Lenmen-Graphene-Infused-Weighted-Shoulders-Christmas/dp/B0CGM2SWK2/ on Jun. 26, 2025. (Year: 2023).*

(Continued)

*Primary Examiner* — F Griffin Hall

(74) *Attorney, Agent, or Firm* — RAYCHAN PATENT FIRM; Raymond Y Chan

(57) ABSTRACT

A heating shawl comprises a shawl body, in which a heating element is arranged; the shawl body comprises a shoulder part and a neck part, and the surfaces of the shoulder part and the neck part which are in contact with the human body are set as contact surfaces, wherein the contact surfaces are provided with heat conducting lines for conducting heat to spread uniformly. The lower hem of the shoulder part is provided with a counterweight structure, which comprises a hollow connecting part and a counterweight filled in the connecting part.

18 Claims, 4 Drawing Sheets

(56) References Cited

U.S. PATENT DOCUMENTS

| | | | | |
|---|---|---|---|---|
| 10,974,018 | B2 * | 4/2021 | Pacheco | A47G 9/007 |
| 2021/0330100 | A1 * | 10/2021 | Ureten | A61N 1/16 |

FOREIGN PATENT DOCUMENTS

| | | | | | |
|---|---|---|---|---|---|
| CN | 106714344 | A | * | 5/2017 | H05B 3/145 |
| CN | 109198746 | A | * | 1/2019 | A61N 5/06 |
| CN | 109495996 | A | * | 3/2019 | A47C 7/383 |
| KR | 20170136876 | A | * | 12/2017 | D21H 25/005 |
| KR | 20180001053 | U | * | 4/2018 | |
| KR | 20240141920 | A | * | 9/2024 | A47C 31/023 |

OTHER PUBLICATIONS

Amazon.com Listing for Graphene-Infused 1Min Fast Heating Pad, with first available date Sep. 5, 2024, retrieved at https://www.amazon.com/Lenmen-Graphene-Infused-Weighted-Shoulders-Christmas/dp/B0DG5DRZWD/ on Jun. 26, 2025. (Year: 2024).*

Amazon.com Listing for Graphene-Infused Heating Pad 3X, with first available date Aug. 25, 2023, retrieved at https:// www.amazon.com/Lenmen-Graphene-Infused-Weighted-Shoulders-Christmas/dp/B0CGM2SWK2/ on Jun. 26, 2025. (Year: 2023) (Year: 2023).*

* cited by examiner

HEATING SHAWL

TECHNICAL FIELD

The present disclosure relates to a shawl, in particular to a heating shawl.

BACKGROUND

The heating shawl, also known as the exothermic shawl or the electric heating shawl, is specially designed for people who suffer from shoulder and neck discomfort due to long-term sedentary office work or special post work. The heating shawl is made of soft and skin-friendly material, which fits the skin and is easy to operate. Whether at home for leisure or office study, it can effectively relieve the pressure on the shoulder and neck, eliminate discomfort and bring a warm and comfortable experience.

The existing US patent No. 20140131341 discloses an "Autonomous Heated Interlining". The self-heating interlining in this patent includes a main heating channel and a secondary heating channel for heating the interlining. However only the interior is heated, and when the shawl is used, the heat transferred to the surface of the shawl is less, the temperature is low, the heating is uneven, and the hot compress physical therapy effect is poor.

Therefore, there is a need to put forward a new type of heating shawl, which can uniformly distribute heat on the whole shawl, enhance the heating effect of shawl, promote blood circulation and effectively relieve muscle fatigue and soreness.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various embodiments of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The present disclosure provides a heating shawl to solve the problem that the heating shawl proposed in the above background can not uniformly distribute heat.

In order to solve the above problems, the present disclosure adopts the following technical solution:

The present disclosure provides a heating shawl, which includes a shawl body, in which a heating element is arranged; the shawl body includes a shoulder part and a neck part, and the surfaces of the shoulder part and the neck part which contact with a human body are set as contact surfaces; the contact surfaces are provided with heat conducting lines for conducting heat to spread uniformly; a lower hem of the shoulder part is provided with a counterweight structure, and the counterweight structure includes a hollow connecting part and a counterweight filled in the connecting part.

The present disclosure further provides a heating shawl, which includes a shawl body, in which a heating element is arranged; one side of the shawl body contacting with a human body is set as a contact surface; the contact surface is provided with heat conducting lines for conducting heat to spread uniformly; and a lower hem of the shawl body is provided with a counterweight structure, and the counterweight structure includes a hollow connecting part and a counterweight filled in the connecting part.

The present disclosure further provides a heating shawl, which includes a shawl body, in which a heating element is arranged; the shawl body includes a shoulder part and a neck part, and the surfaces of the shoulder part and the neck part which contact with a human body are set as contact surfaces; the contact surfaces are provided with a heat conducting layer for conducting heat to spread uniformly; a counterweight is arranged on the shawl body for the contact surface to be closely attached to the human body.

BRIEF DESCRIPTION OF DRAWINGS

In order to explain the technical scheme of this application more clearly, the drawings needed in the implementation will be briefly introduced below. Obviously, the drawings described below are only some implementations of this application. For those skilled in the art, other drawings can be obtained according to these drawings without creative work.

Figure 1:
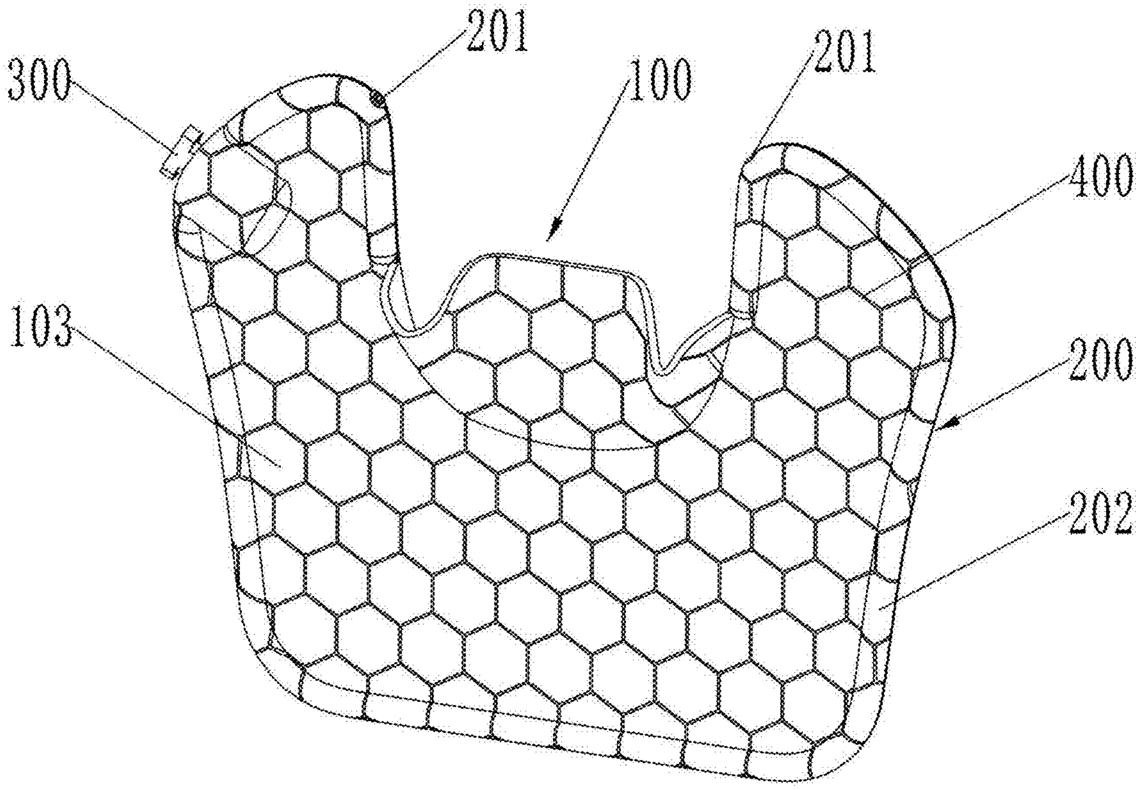
FIG. 1 is a schematic diagram of the three-dimensional structure of the present disclosure in an unfolded state.

Reference signs: Shawl body (100); Shoulder part (101); Neck part (102); Contact surface (103); Counterweight structure (200); Connector (201); Connecting part (202); Counterweight (203); Power supply interface (300); Heat conducting lines (400); Heating element (500).

DESCRIPTION OF EMBODIMENTS

In describing the preferred embodiments, specific terminology will be resorted to for the sake of clarity. It is to be understood that each specific term includes all technical equivalents which operate in a similar manner to accomplish a similar purpose.

While various aspects and features of certain embodiments have been summarized above, the following detailed description illustrates a few exemplary embodiments in further detail to enable one skilled in the art to practice such embodiments. Reference will now be made in detail to embodiments of the inventive concept, examples of which are illustrated in the accompanying drawings. The accompanying drawings are not necessarily drawn to scale. The described examples are provided for illustrative purposes and are not intended to limit the scope of the invention. It should be understood, however, that persons having ordinary skill in the art may practice the inventive concept without these specific details.

It will be understood that, although the terms first, second, etc. may be used herein to describe various elements, these elements should not be limited by these terms. These terms are only used to distinguish one element from another. For example, a first attachment could be termed a second attachment, and, similarly, a second attachment could be termed a first attachment, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

As used in the description of the inventive concept and the appended claims, the singular forms "a," "an," and "the" are intended to include the plural forms as well, unless the context clearly indicates other.

Embodiment 1

As shown in FIG. 1 to FIG. 5, the present disclosure provides a heating shawl, which includes a shawl body 100. The shawl body 100 includes a shoulder part 101 and a neck part 102, and the surfaces of the shoulder part 101 and the neck part 102 which contact with the human body are set as a contact surface 103. The contact surface 103 is provided with heat conducting lines 400, and a heating element 500 is arranged in the shawl body 100. A counterweight structure 200 is arranged at the lower hem of the shoulder part 101, and the counterweight structure 200 includes a hollow connecting part 202 and a counterweight 203 filled in the connecting part.

As shown in FIG. 1, in this embodiment, the shoulder part 101 includes a connector 201.

In one embodiment, the connector 201 includes a male buckle and a female buckle, and the connection is realized through the male buckle and the female buckle that are mutually buckled. There is a raised part on the male buckle and a corresponding groove or hole on the female buckle. The connection between them may be realized by only aligning male buckle with the groove or hole of the female buckle and then pressing. Similarly, to release the connection, it only needs to pull them apart. Once buckled, the connector 201 can fix the shawl on the shoulder part, ensuring that the shawl will not loosen or fall off and keep a certain temperature.

In another embodiment of the connector 201 (not shown), the connector 201 may also be two magnets, each of which is circular or rectangular (the specific shapes can be varied). These two magnets are embedded in the edge positions on both sides of the shoulder part of the shawl, and the two magnets are of moderate size and provide stable adsorption force. In the positional relationship, the N pole of one magnet is opposite to the S pole of the other magnet, and when the two magnets are getting close to each other, the adsorption can be automatically and quickly completed. This non-contact connection mode avoids physical wear caused by frequent locking and unlocking, thus prolonging the service life of the shawl. In addition, the connection of two magnets will not produce noise.

In another embodiment of the connector 201 (not shown), the connector 201 may also be a hook and loop, and has a fiber surface and a bristle surface, respectively. One side of the shoulder part 101 is provided with a fiber surface, and the other side of the shoulder part 101 is provided with a bristle surface. The fiber surface and the bristle surface are bonded to realize the connection of the shoulder part. The connection mode of hook and loop is simple and quick, with good wear resistance and durability, and it can be opened and closed for many times without damage. The connection position of fiber surface and bristle surface may be adjusted to meet different use requirements.

As shown in FIGS. 2 to 5, in this embodiment, a heating element 500 is arranged inside the shawl body 100, and the heating element 500 can output a stable temperature. The shoulder part 101 is provided with a power supply interface 300, and the heating element 500 is electrically connected with the power supply interface 300. The power supply interface 300 is arranged on the shoulder part 101 at a position that may be easily accessed, which is convenient for charging at any time during use and ensures the continuous use of the heating shawl.

In other embodiments (not shown), the shawl body 100 is internally provided with hot channels, and the hot channels are uniformly laid in the whole shawl body 100. The hot channels adopt a hollow structure, which can contain heat-conducting colloid and achieve the function of heating the shawl. A colloid inlet is arranged on the left side of the shoulder part 101, and a colloid outlet is arranged on the right side of the shoulder part 101, so that the heat-conducting colloid can circulate and continuously pass through the hot channels, and the shawl is always kept at an appropriate temperature.

Figure 2:
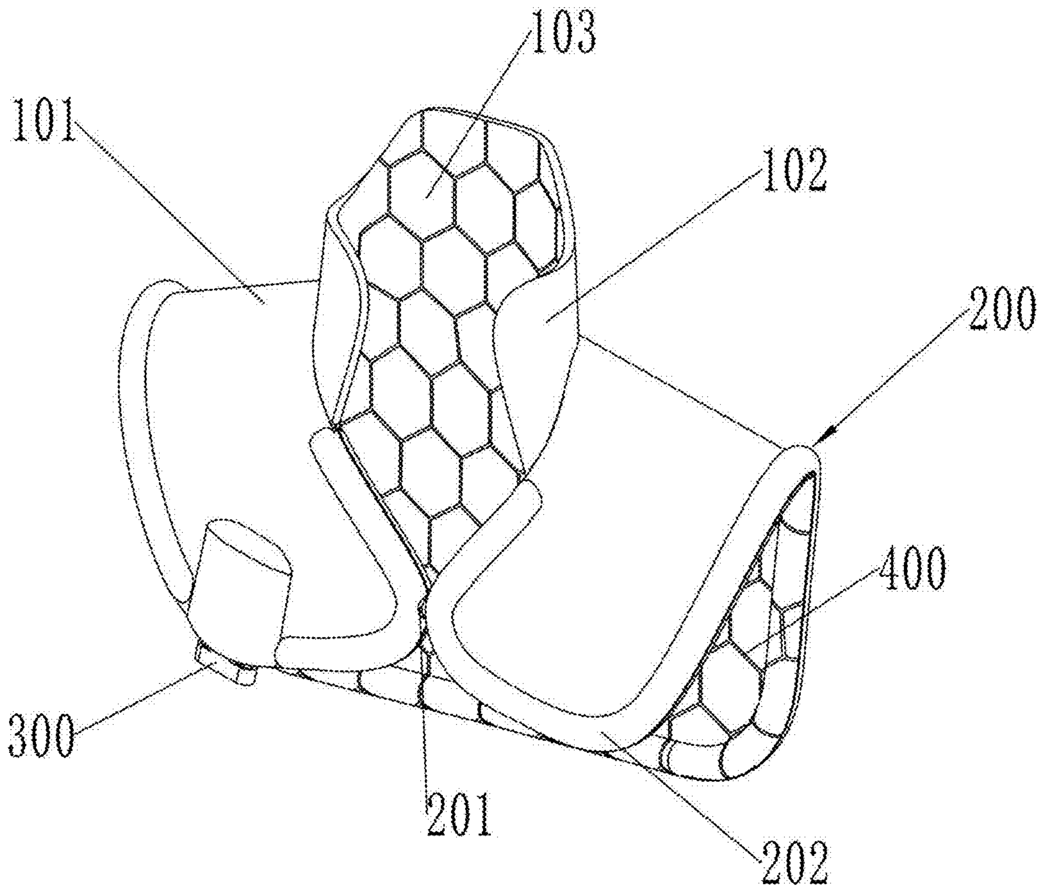
FIG. 2 is a schematic diagram of the three-dimensional structure of the present disclosure in an buckled state.

As shown in FIG. 1 to FIG. 2, in this embodiment, the shawl body 100 includes a shoulder part 101 and a neck part 102, and the shoulder part 101 and the neck part 102 are integrated structures, which naturally transition and conform to the contour of the human body. The shoulder part 101 is wide, covering and wrapping the whole shoulder part, while the neck part 102 is slender, providing warmth around the neck part. The sides of shoulder part 101 and neck part 102 that directly contacts with human body are called contact surfaces 103.

In this embodiment, the contact surface 103 is made of a plush material. The fibers of the plush material are fine and fluffy, which can form an air layer and effectively isolate the cold outside. At the same time, its good elasticity and adaptability enable the shawl to conform to the human body curve, reduce air convection, and thus enhance the heating effect.

In other embodiments (not shown), the contact surfaces 103 on the shoulder part 101 and the neck part 102 are made of cashmere-like, polar fleece and microfiber. Cashmere-like fabric is smooth, soft and elastic, rich in color, low in cost, easy to handle, and can provide a comfortable touch. Polar fleece is lighter in weight, strong in warmth retention, soft in texture, and good in breathability and perspiration. Microfiber has excellent softness and warmth retention, can quickly absorb and distribute moisture, keep skin dry, and is wear-resistant and wrinkle-resistant.

Figure 3:
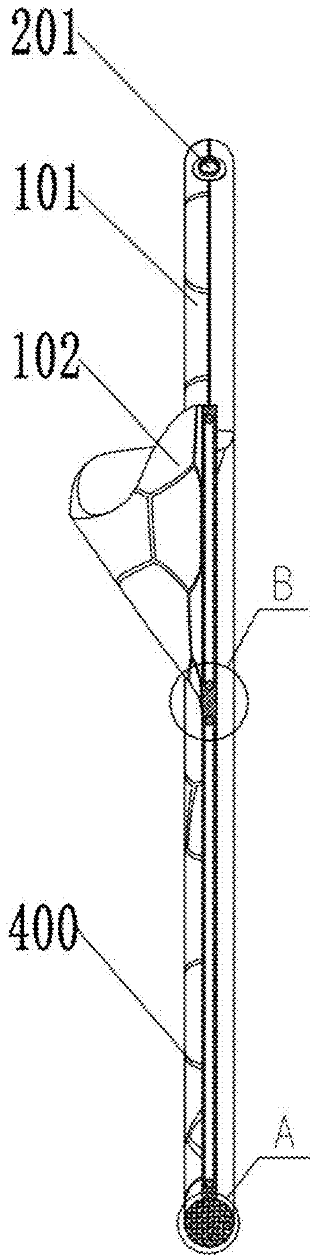
FIG. 3 is a schematic sectional view of the present disclosure.
Figure 4:
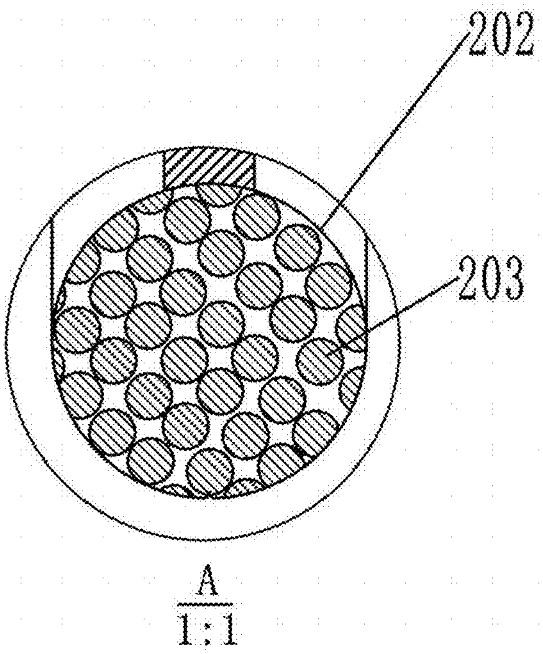
FIG. 4 is an enlarged schematic view of part A of FIG. 3 in the present disclosure.
Figure 5:
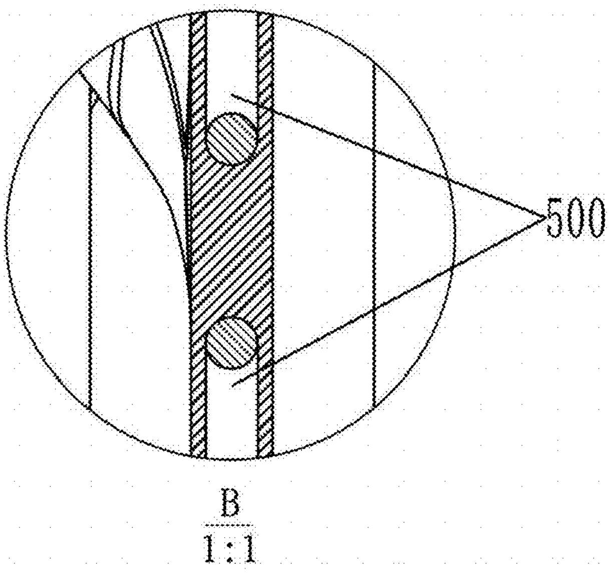
FIG. 5 is an enlarged schematic view of part B of FIG. 3 in the present disclosure.

As shown in FIGS. 2 to 4, in this embodiment, the heating shawl includes a counterweight structure 200, and the counterweight structure 200 includes a connecting part 202 and a counterweight 203.

By arranging the counterweight structure 200, when the heating shawl is used, the lower hem of the shoulder part 101 is ensured to be vertical and in contact with the human body, so that the contact surface 103 can be closely attached to the human body, thereby improving the hot compress effect of the heating shawl.

In this embodiment, the shawl body 100 and the connecting part 202 are integrally formed, which makes the whole heating shawl more compact. In addition, the heat conducting lines 400 of the heating shawl uniformly cover the contact surfaces 103, which not only improves the heat conduction efficiency, but also makes the heat distribution more uniform.

In this embodiment, the heat conducting lines 400 of the heating shawl are made of a graphene material. Graphene is a nano-material with strong thermal properties and high stability. In addition to hexagonal patterns, the heat conducting lines 400 may also be circles, triangles, rectangles and polygons, which are closely connected with each other to form a uniform and stable heat conduction network. The heat conduction network enables the heat energy to be transmitted quickly and distributed uniformly on the contact surfaces 103, ensuring that the shoulder and neck of the body touch the shawl and can feel the balanced heat energy conduction. Moreover, through the heat conducting lines 400 with different shapes, the heat conducting lines 400 have different heat conduction densities, so that the heating shawls with different heat conduction densities are suitable for different people and meet the needs of different people.

In other embodiments (not shown), the heat conducting lines 400 on the contact surfaces 103 may also be heat conducting pads made of carbon fibers, which have good heat conducting performance and can conduct heat. In the heating shawl, this high thermal conductivity can ensure that the heat can be quickly and uniformly distributed to all parts of the shawl. At the same time, carbon fiber has the characteristics of low density and high strength. The heat conductive gasket made of carbon fiber has good mechanical strength and durability while maintaining light weight. In addition, the carbon fiber heat-conducting gasket has certain flexibility, which not only increases the contact area of the heat-conducting surface and improves the heat-conducting efficiency, but also makes it more suitable for the human body when the shawl is worn, and enhances the comfort and warm-keeping effect.

In this embodiment, the heat conducting lines 400 extend to the connecting part 202, so that the connecting part 202 can also uniformly transfer heat. In one embodiment of the counterweight 203, the counterweight 203 is a far-infrared magnet and is filled in the hollow connecting part 202. When the heat conducting lines 400 transfer heat to the connecting part 202, the far-infrared magnet will be heated and generate far infrared rays. The deep penetration force of the far-infrared rays can reach the depths of muscle joints, so that the far-infrared magnet can improve joint pain and relieve muscle fatigue. Far infrared rays may also penetrate deep into the human body, directly act on the painful parts, promote local blood circulation, accelerate the absorption and dissipation of inflammatory exudates, and relieve pain.

In other embodiments (not shown), the counterweight 203 may also be mineral sand (quartz sand) or mineral stone (volcanic stone), and these particles are circular or irregular in shape and uniformly distributed in the connecting part 202 of the heating shawl. These counterweights are fixed in the counterweight structure of the shawl through a specific process to form a counterweight layer. Mineral sand or mineral stone not only has high density, but also has certain thermal insulation performance, which can assist in the heating effect to a certain extent.

In other embodiments (not shown), the shawl body 100 and the connecting part 202 are detachably connected, and the detachable connection between the shawl body 100 and the connecting part 202 includes a snap fastener structure or a zipper structure. Both structures have connection stability, and the shawl will not fall off when worn on the human body. The detachable connection between the connecting part 202 and the shawl body 100 improves the flexibility of use, and is convenient for installation and disassembly, and at the same time saves space and is convenient for storage.

In one of the above-mentioned embodiments (not shown), the shawl body 100 and the connecting part 202 are connected by magnetic buckles. The magnetic buckle connection fixes the connecting part 202 and the shawl body 100 together by the attraction of magnets. The connection mode of the magnetic buckle is fast and convenient, and the shawl material will not be damaged. When the magnetic buckle is connected, it relies on magnetic force and adsorption force to avoid mechanical wear and damage, so that the magnetic buckle has a longer service life, and is more stable and reliable in the use process.

In one of the above embodiments (not shown), a hook and loop connection is adopted between the shawl body 100 and the connecting part 202. Hook and loop, also known as velcro tape or adhesive tape, consists of a hook surface with fine and soft fiber fluff and a rough surface with stiff and fine plastic. When in use, the hook surface and the rough surface can be bonded only by gently pressing, and the combination and separation are simple and quick, and can be used repeatedly.

To sum up, by arranging the heat conducting lines 400 on the contact surface 103, the present disclosure can allow the heating shawl to uniformly distribute heat throughout the shawl, enhance the heating effect of the shawl, promote blood circulation, and effectively relieve muscle fatigue and soreness.

Embodiment 2

The present disclosure provides a heating shawl, which includes a shawl body 100, and a heating element 500 is arranged in the shawl body 100. The shawl body 100 includes a shoulder part 101 and a neck part 102, and the surfaces of the shoulder part 101 and the neck part 102 which contact with the human body are set as contact surfaces 103. The contact surfaces 103 are provided with heat conducting layers for conducting heat to spread uniformly. The shawl body 100 is provided with a counterweight for the contact surfaces to be closely attached to the human body.

The difference between Embodiment 2 and Embodiment 1 is that (not shown), the counterweight is spherical particles and uniformly filled in the shawl body 100. Therefore, in this way, the whole shawl body 100 has a weight-bearing effect, ensuring that the contact surface 103 of the shoulder part 101 and the neck part 102 can closely contact with the human body, and improving the physical therapy effect of hot compress.

It is certain that in this embodiment, in order to ensure that the lower hem position of the shoulder part 101 can still be in close contact with the human body, a strap (not shown) may also be provided at the lower hem position of the shoulder part 101, and the shawl body 100 may be bound to the human body through the strap. This can prevent the shawl body 100 from shaking during the user's activities, and ensure that the contact surfaces 103 of the shawl body 100 are still in close contact with the human body.

The technical means disclosed in the scheme of the present invention are not limited to the technical means disclosed in the above embodiments, but also include the technical scheme composed of any combination of the above technical features. It should be pointed out that for those skilled in the art, several improvements and embellishments can be made without departing from the principle of the present invention, and these improvements and embellishments are also regarded as the protection scope of the present invention.

The invention has now been described in detail for the purposes of clarity and understanding. However, those skilled in the art will appreciate that certain changes and modifications may be practiced within the scope of the appended claims.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A heating shawl, comprising;

a shawl body comprising a heating element and heat conducting lines, the heating element and the heat conducting lines arranged in the shawl body, wherein the shawl body comprises a shoulder part and a neck part, each of the shoulder part and the neck part comprising contact surfaces configured for making contact with a human body;

the heat conducting lines are uniformly arranged on the contact surfaces of the shoulder part and the neck part and configured for conducting heat to spread uniformly;

a lower hem of the shoulder part is provided with a counterweight structure, and the counterweight structure comprises a hollow connecting part and a counterweight filled in the hollow connecting part, wherein the counterweight comprises quartz sand or volcanic stone, wherein the heat conducting lines extend to the hollow connecting part such that heat is conducted to the counterweight structure.

2. The heating shawl according to claim 1, wherein the shawl body further comprises a power supply interface, and the power supply interface is arranged on the shoulder part.

3. The heating shawl according to claim 2, wherein the power supply interface is electrically connected with the heating element, and the power supply interface provides electric energy for the heating element.

4. The heating shawl according to claim 1, wherein the shoulder part comprises a connector arranged on the counterweight structure; the connector is configured for connecting the shoulder part.

5. The heating shawl according to claim 4, wherein the connector is a fastener, the fastener is divided into a male buckle and a female buckle, and the male buckle and the female buckle are buckled to connect the shoulder part.

6. The heating shawl according to claim 4, wherein the connector is a magnetic member, the magnetic member is divided into an N pole and an S pole, and the N pole and the S pole are attracted together to connect the shoulder part.

7. The heating shawl according to claim 1, wherein a material of the heat conducting lines is graphene.

8. The heating shawl according to claim 1, wherein a material of the contact surface is a plush material.

9. A heating shawl, comprising:

a shawl body comprising a heating element and heat conducting lines, wherein the heating element and the heat conducting lines are arranged in the shawl body, wherein one side of the shawl body is configured for contacting with a human body and is set as a contact surface;

the heat conducting lines are uniformly arranged on the contact surface and configured for conducting heat to spread uniformly;

a lower hem of the shawl body is provided with a counterweight structure, and the counterweight structure comprises a hollow connecting part and a counterweight filled in the hollow connecting part;

the counterweight is a far-infrared magnet;

the heat conducting lines extend to the hollow connecting part and contact the far-infrared magnet.

10. The heating shawl according to claim 9, wherein the hollow connecting part is detachably connected with the shawl body by a detachable connection.

11. The heating shawl according to claim 10, wherein the detachable connection comprises a snap fastener connection or a zipper connection.

12. The heating shawl according to claim 9, wherein the hollow connecting part is integrally formed with the shawl body.

13. The heating shawl according to claim 9, wherein the counterweight is in a shape of spherical particles or strips.

14. The heating shawl according to claim 13, wherein the counterweight has thermal conductivity.

15. A heating shawl, comprising:

a shawl body comprising a heating element and a heat conducting layer, the heating element and the heat conducting layer arranged in the shawl body, wherein the shawl body comprises a shoulder part and a neck part, each of the shoulder part and the neck part comprising contact surfaces configured for making contact with a human body;

the heat conducting layer is uniformly arranged on the contact surfaces and configured for conducting heat to spread uniformly;

a counterweight is arranged on the shawl body and configured for causing the contact surfaces to be closely attached to the human body;

the counterweight is a far-infrared magnet;

the heat conducting layer extends to and contacts the far-infrared magnet.

16. The heating shawl according to claim 15, wherein the heat conducting layer is heat conducting lines, and a material of the heat conducting lines is graphene.

17. The heating shawl according to claim 16, wherein the heat conducting lines have hexagons which are connected with each other and uniformly cover the contact surface.

18. The heating shawl according to claim 15, wherein the counterweight is spherical particles that are uniformly filled in the shawl body.

* * * * *